(12) United States Patent
Twomey et al.

(10) Patent No.: US 9,060,780 B2
(45) Date of Patent: Jun. 23, 2015

(54) METHODS OF MANUFACTURING SHAFTS FOR SURGICAL INSTRUMENTS

(75) Inventors: John R. Twomey, Longmont, CO (US); James D. Allen, IV, Broomfield, CO (US); Ryan C. Artale, Boulder, CO (US); Dennis W. Butcher, Longmont, CO (US); Russell D. Hempstead, Lafayette, CO (US); Glenn A. Horner, Boulder, CO (US); Jessica E. C. Olson, Frederick, CO (US); Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 904 days.

(21) Appl. No.: 13/249,024

(22) Filed: Sep. 29, 2011

(65) Prior Publication Data

US 2013/0085491 A1    Apr. 4, 2013

(51) Int. Cl.
*A61B 18/00* (2006.01)
*A61B 18/14* (2006.01)
*A61B 17/295* (2006.01)
*A61B 17/29* (2006.01)

(52) U.S. Cl.
CPC ......... *A61B 18/1445* (2013.01); *Y10T 29/4998* (2015.01); *Y10T 29/49826* (2015.01); *A61B 17/295* (2013.01); *A61B 2017/2901* (2013.01); *A61B 2017/2902* (2013.01); *A61B 2018/1455* (2013.01)

(58) Field of Classification Search
CPC ....................... A61B 18/1445; Y10T 29/49826
USPC .................................... 29/434; 606/42, 46, 48
See application file for complete search history.

(56) References Cited

U.S. PATENT DOCUMENTS

| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| D343,453 | S | 1/1994 | Noda |
| D348,930 | S | 7/1994 | Olson |
| D349,341 | S | 8/1994 | Lichtman et al. |
| D354,564 | S | 1/1995 | Medema |

(Continued)

FOREIGN PATENT DOCUMENTS

| CN | 201299462 | 9/2009 |
| DE | 2415263 A1 | 10/1975 |

(Continued)

OTHER PUBLICATIONS

Int'l Search Report EP 07 021646.0 dated Mar. 20, 2008.

(Continued)

*Primary Examiner* — Jermie Cozart

(57) ABSTRACT

A surgical instrument includes a shaft formed via extrusion. The shaft has one or more lumens extending therethrough. The lumen(s) each define a cross-sectional configuration. An end effector assembly is coupled to a distal end of the shaft. One or more components are coupled to the end effector assembly. The component(s) extend proximally from the end effector into the lumen(s) of the shaft. One or more of the components is formed via stamping. The component(s) define a cross-sectional configuration substantially complementary to the cross-section configuration of the lumen into which they extend.

6 Claims, 4 Drawing Sheets

(56) References Cited

U.S. PATENT DOCUMENTS

| | | |
|---|---|---|
| D358,887 S | 5/1995 | Feinberg |
| 5,482,054 A | 1/1996 | Slater et al. |
| D384,413 S | 9/1997 | Zlock et al. |
| 5,766,170 A | 6/1998 | Eggers |
| H1745 H | 8/1998 | Paraschac |
| D402,028 S | 12/1998 | Grimm et al. |
| 5,849,022 A | 12/1998 | Sakashita et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,066,102 A * | 5/2000 | Townsend et al. ............ 600/564 |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 6,964,662 B2 * | 11/2005 | Kidooka .......................... 606/52 |
| 6,997,931 B2 | 2/2006 | Sauer et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 2002/0099369 A1 | 7/2002 | Schulze |
| 2006/0161190 A1 * | 7/2006 | Gadberry et al. ............. 606/174 |
| 2008/0097293 A1 * | 4/2008 | Chin et al. ................. 604/95.04 |
| 2009/0088738 A1 | 4/2009 | Guerra et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 98/14124 | 4/1998 |
| WO | 9945847 A1 | 9/1999 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/040483 A1 | 4/2008 |

OTHER PUBLICATIONS

Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.

(56) References Cited

OTHER PUBLICATIONS

Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 10 185386.9 dated Jan. 10, 2011.
Int'l Search Report EP 10 185405.7 dated Jan. 5, 2011.
Int'l Search Report EP 11 168419.7 dated Oct. 20, 2011.
U.S. Appl. No. 08/926,869, James G. Chandler.
U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
U.S. Appl. No. 13/050,182, Glenn A. Horner.
U.S. Appl. No. 13/072,945, Patrick L. Dumbauld.
U.S. Appl. No. 13/080,383, David M. Garrison.
U.S. Appl. No. 13/085,144, Keir Hart.
U.S. Appl. No. 13/091,331, Jeffrey R. Townsend.
U.S. Appl. No. 13/102,573, John R. Twomey.
U.S. Appl. No. 13/102,604, Paul E. Ourada.
U.S. Appl. No. 13/108,093, Boris Chernov.
U.S. Appl. No. 13/108,129, Boris Chernov.
U.S. Appl. No. 13/108,152, Boris Chernov.
U.S. Appl. No. 13/108,177, Boris Chernov.
U.S. Appl. No. 13/108,196, Boris Chernov.
U.S. Appl. No. 13/108,441, Boris Chernov.
U.S. Appl. No. 13/108,468, Boris Chernov.
U.S. Appl. No. 13/111,642, John R. Twomey.
U.S. Appl. No. 13/111,678, Nikolay Kharin.
U.S. Appl. No. 13/113,231, David M. Garrison.
U.S. Appl. No. 13/157,047, John R. Twomey.
U.S. Appl. No. 13/162,814, Barbara R. Tyrrell.
U.S. Appl. No. 13/166,477, Daniel A. Joseph.
U.S. Appl. No. 13/166,497, Daniel A. Joseph.
U.S. Appl. No. 13/179,919, Russell D. Hempstead.
U.S. Appl. No. 13/179,960, Boris Chernov.
U.S. Appl. No. 13/179,975, Grant T. Sims.
U.S. Appl. No. 13/180,018, Chase Collings.
U.S. Appl. No. 13/183,856, John R. Twomey.
U.S. Appl. No. 13/185,593, James D. Allen, IV.
U.S. Appl. No. 13/204,841, Edward J. Chojin.
U.S. Appl. No. 13/205,999, Jeffrey R. Unger.
U.S. Appl. No. 13/212,297, Allan J. Evans.
U.S. Appl. No. 13/212,308, Allan J. Evans.
U.S. Appl. No. 13/212,329, Allan J. Evans.
U.S. Appl. No. 13/212,343, Duane E. Kerr.
U.S. Appl. No. 13/223,521, John R. Twomey.
U.S. Appl. No. 13/227,220, James D. Allen, IV.
U.S. Appl. No. 13/228,742, Duane E. Kerr.
U.S. Appl. No. 13/231,643, Keir Hart.
U.S. Appl. No. 13/234,357, James D. Allen, IV.
U.S. Appl. No. 13/236,168, James D. Allen, IV.
U.S. Appl. No. 13/236,271, Monte S. Fry.
U.S. Appl. No. 13/243,628, William Ross Whitney.
U.S. Appl. No. 13/247,778, John R. Twomey.
U.S. Appl. No. 13/247,795, John R. Twomey.
U.S. Appl. No. 13/248,976, James D. Allen, IV.

(56) References Cited

OTHER PUBLICATIONS

U.S. Appl. No. 13/249,013, Jeffrey R. Unger.
U.S. Appl. No. 13/249,024, John R. Twomey.
U.S. Appl. No. 13/251,380, Duane E. Kerr.
U.S. Appl. No. 13/277,373, Glenn A. Horner.
U.S. Appl. No. 13/277,926, David M. Garrison.
U.S. Appl. No. 13/277,962, David M. Garrison.
U.S. Appl. No. 13/293,754, Jeffrey M. Roy.
U.S. Appl. No. 13/306,523, David M. Garrison.
U.S. Appl. No. 13/306,553, Duane E. Kerr.
U.S. Appl. No. 13/308,104, John R. Twomey.
U.S. Appl. No. 13/312,172, Robert J. Behnke, II.
U.S. Appl. No. 13/324,863, William H. Nau, Jr.
U.S. Appl. No. 13/344,729, James D. Allen, IV.
U.S. Appl. No. 13/355,829, John R.Twomey.
U.S. Appl. No. 13/357,979, David M. Garrison.
U.S. Appl. No. 13/358,136, James D. Allen, IV.
U.S. Appl. No. 13/360,925, James H. Orszulak.
U.S. Appl. No. 13/400,290, Eric R. Larson.
U.S. Appl. No. 13/404,435, Kim V. Brandt.
U.S. Appl. No. 13/404,476, Kim V. Brandt.
U.S. Appl. No. 13/412,879, David M. Garrison.
U.S. Appl. No. 13/412,897, Joanna Ackley.
U.S. Appl. No. 13/421,373, John R. Twomey.
U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/464,569, Duane E. Kerr.
U.S. Appl. No. 13/466,274, Stephen M. Kendrick.
U.S. Appl. No. 13/467,767, Duane E. Kerr.
U.S. Appl. No. 13/470,543, Sean T. Dycus.
U.S. Appl. No. 13/470,775, James D. Allen, IV.
U.S. Appl. No. 13/470,797, John J. Kappus.
U.S. Appl. No. 13/482,589, Eric R. Larson.
U.S. Appl. No. 13/483,733, Dennis W. Butcher.
U.S. Appl. No. 13/488,093, Kristin D. Johnson.
U.S. Appl. No. 13/491,853, Jessica E. Olson.
U.S. Appl. No. 13/537,517, David N. Heard.
U.S. Appl. No. 13/537,577, Tony Moua.
U.S. Appl. No. 13/550,322, John J. Kappus.
U.S. Appl. No. 13/571,055, Paul Guerra.
U.S. Appl. No. 13/571,821, Joseph D. Bucciaglia.
U.S. Appl. No. 13/584,194, Sean T. Dycus.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

(56) References Cited

OTHER PUBLICATIONS

Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Partial European Search Report dated Mar. 31, 2015, issued in European Appln. No. 12 18 4993.

* cited by examiner

METHODS OF MANUFACTURING SHAFTS FOR SURGICAL INSTRUMENTS

BACKGROUND

The present disclosure relates to surgical instruments and, more particularly, to surgical forceps for grasping, sealing, and/or dividing tissue.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

An endoscopic surgical forceps typically includes an elongated shaft having an end effector assembly, e.g., a pair of jaw members, disposed at the distal end thereof. The elongated shaft permits the surgeon to insert the end effector assembly through a relatively small access opening in the body to the internal surgical site, while the housing of the endoscopic forceps remains disposed externally of the surgical site. The surgeon may then control the operation of the end effector assembly, e.g., to grasp, seal, and/or divide tissue, by manipulating the housing. As can be appreciated, numerous mechanical and electrical connections extend through the shaft to permit the surgeon to operate the end effector assembly by manipulating mechanical and/or electrical components coupled to the housing.

SUMMARY

In accordance with one embodiment of the present disclosure, a surgical instrument is provided. The surgical instrument includes a shaft formed via extrusion. The shaft has one or more lumens extending therethrough. The lumen(s) defines a cross-sectional configuration. An end effector assembly is coupled to a distal end of the shaft. One or more components is coupled to the end effector assembly and extends proximally from the end effector assembly through the lumen(s) of the shaft. One or more of the components is formed via stamping and defines a cross-sectional configuration substantially complementary to the cross-section configuration of the lumen into which it extends.

In one embodiment, one of the components is a drive bar configured to translate through one of the lumens of the shaft to transition the end effector assembly between a first condition and a second condition.

In another embodiment, a second stamped component is disposed (partially) within the drive bar. The second component is configured to translate relative to the shaft and the end effector assembly to perform an operation at the end effector assembly.

In still another embodiment, one (or more) of the components is a mounting flange for coupling the end effector assembly to the shaft.

In yet another embodiment, a wire lumen (or wire lumens) extends through the shaft. The wire lumen is configured to receive an electrical wire therethrough for supplying energy to the end effector assembly.

In still yet another embodiment, the shaft is formed from an electrically-insulative material, e.g., a plastic.

In accordance with the present disclosure, another embodiment of a surgical instrument is provided. The surgical instrument includes a metal outer sleeve defining an internal passageway and a plastic inner shaft disposed within the outer sleeve that substantially fills the internal passageway of the outer sleeve. The inner shaft is formed via molding and includes one or more lumens extending therethrough. The lumen(s) defines a cross-sectional shape different from the cross-sectional shape of the internal passageway of the outer sleeve. An end effector assembly is coupled to a distal end of the inner shaft. One ore more components is coupled to the end effector assembly and extends proximally from the end effector assembly into the lumen(s) of the inner shaft.

In one embodiment, one (or more) of the components is a drive bar configured to translate through one of the lumens of the inner shaft to transition the end effector assembly between a first condition and a second condition.

In another embodiment, the shaft includes one or more wire lumens extending therethrough. The wire lumen(s) is configured to receive an electrical wire therethrough for supplying energy to the end effector assembly.

In still another embodiment, the inner shaft is formed via injection molding. Alternatively, the inner shaft may be formed via insert molding.

A method of manufacturing a surgical instrument is also provided in accordance with the present disclosure. The method includes forming a shaft via extrusion such that the shaft includes one or more lumen extending therethrough that are configured to receive one or more substantially complementary-shaped components therein. The method further includes forming the substantially complementary-shaped component(s) via stamping.

In one embodiment, the method further includes coupling an end effector assembly to the shaft via one or more of the components. More specifically, a mounting flange(s) may be engaged within one of the lumens of the shaft. The mounting flange(s) include the end effector assembly coupled thereto.

In another embodiment, one of the components is a drive bar configured to translate through one of the lumens of the shaft to transition the end effector assembly between a first condition and a second condition.

In another embodiment, the method further includes inserting one or more electrical wires through the lumen(s) of the shaft. The electrical wire(s) is configured to transmit electrosurgical energy through the shaft.

BRIEF DESCRIPTION OF THE DRAWINGS

Various embodiments of the present disclosure are described herein with reference to the drawings wherein.

DETAILED DESCRIPTION

Figure 1:
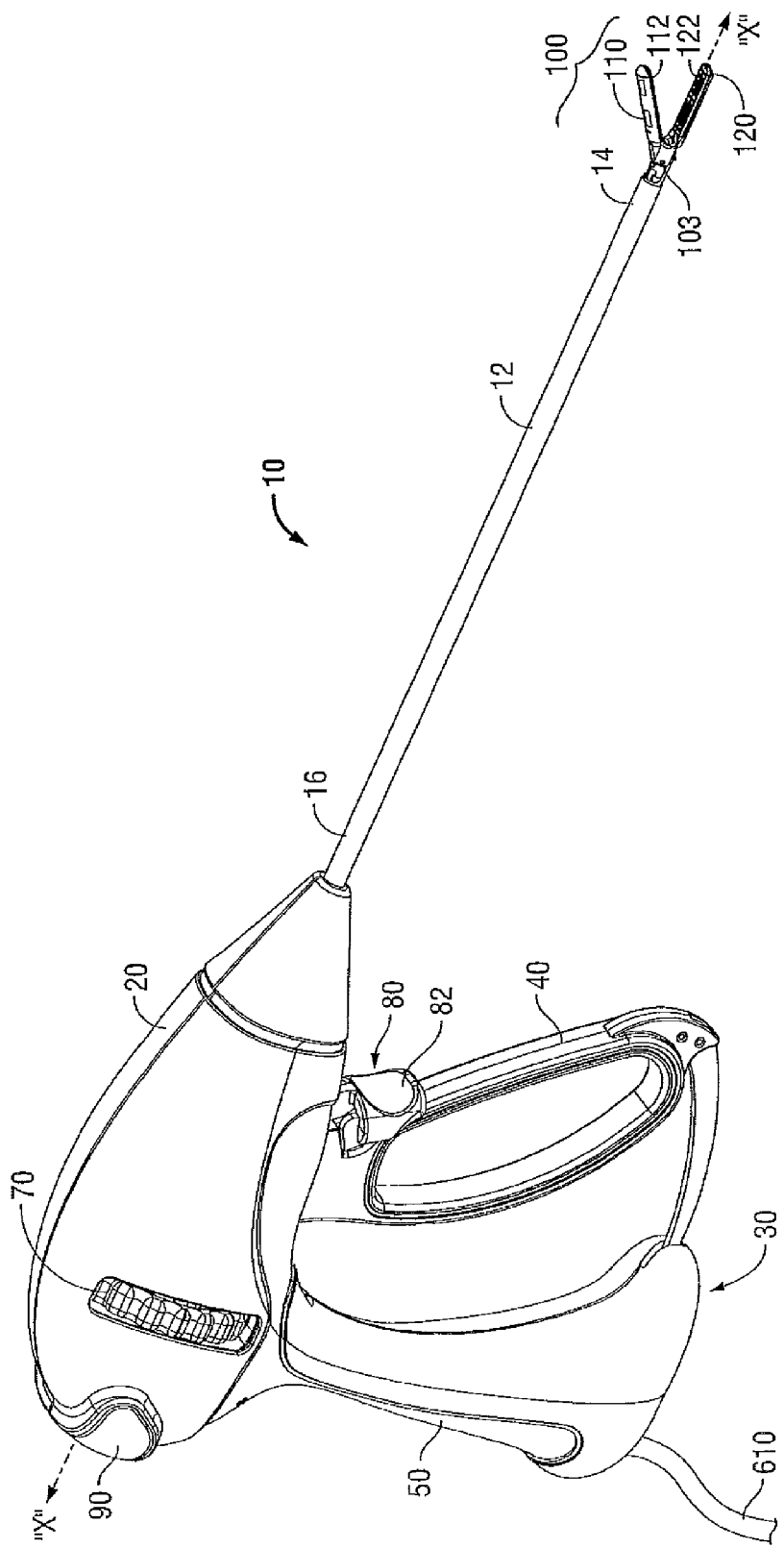
FIG. 1 is a front, perspective view of a surgical forceps provided in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Referring now to FIG. 1, a forceps 10 configured for use in connection with endoscopic surgical procedures is shown. Forceps 10 is one example of a shaft-based surgical instrument incorporating the features of the present disclosure. As can be appreciated, the presently disclosed features detailed below are equally applicable to other shaft-based surgical instruments and are described with reference to forceps 10 for exemplary purposes only. Obviously, different electrical and mechanical connections and considerations apply to each particular type of instrument, however, the novel aspects of the present disclosure remain generally consistent with respect to most shaft-based surgical instruments.

With continued reference to FIG. 1, forceps 10 defines a longitudinal axis "X-X" and includes a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) 612 (FIG. 3C) extending therethrough that has sufficient length to extend through shaft 12 in order to provide electrical energy to the end effector assembly 100, e.g., upon activation of activation switch 90.

Continuing with reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about longitudinal axis "X-X" to rotate end effector assembly 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of the jaw members 110 and 120 includes an opposed electrically conductive tissue-sealing plate 112, 122, respectively. End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12. In some embodiments, a knife assembly 180 (FIGS. 2A-2C) is disposed within shaft 12 and a knife channel 115, 125 (FIGS. 2A-2C) is defined within one or both of jaw members 110, 120, respectively, to permit reciprocation of a knife blade 182 (FIG. 2A-2C) therethrough, e.g., via activation of a trigger 82 of trigger assembly 80.

Referring still to FIG. 1, moveable handle 40 of handle assembly 30 is ultimately connected to a drive assembly including a drive bar 130 (FIGS. 3B-3C) that, together, mechanically cooperate to impart movement of jaw members 110 and 120 between a spaced-apart position (FIG. 2A) and an approximated position (FIGS. 2B-2C) to grasp tissue disposed between sealing plates 112 and 122 of jaw members 110, 120, respectively. As shown in FIG. 1, moveable handle 40 is initially spaced-apart from fixed handle 50 and, correspondingly, jaw members 110, 120 are biased in the spaced-apart position. Moveable handle 40 is actuatable from this initial position to a depressed position corresponding to the approximated position of jaw members 110, 120 (see FIGS. 2B-2C).

Figure 2A:
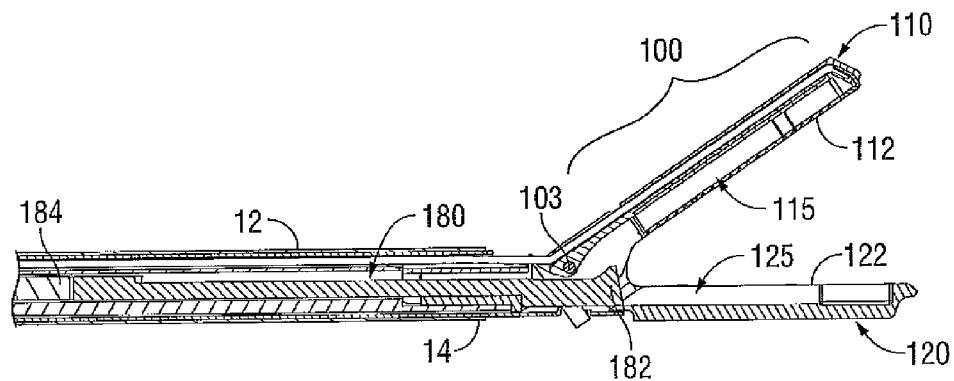
FIG. 2A is a longitudinal, cross-sectional view of an end effector assembly of the forceps of FIG. 1 with jaw members of the end effector assembly disposed in a spaced-apart position.
Figure 2B:
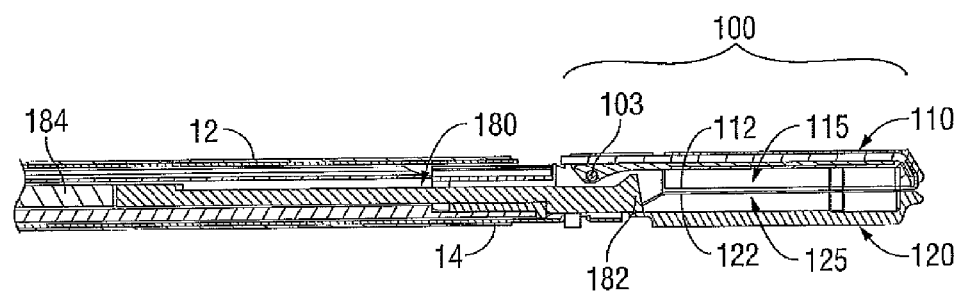
FIG. 2B is a longitudinal, cross-sectional view of the end effector assembly of FIG. 2A with the jaw members disposed in an approximated position and with a knife blade disposed in a retracted position.
Figure 2C:
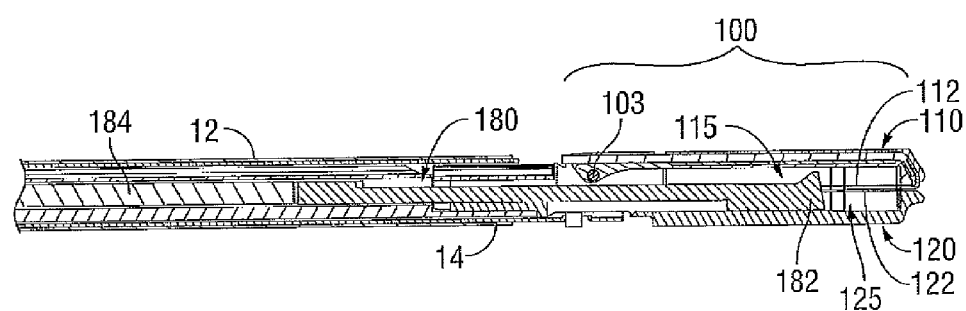
FIG. 2C is a longitudinal, cross-sectional view of the end effector assembly of FIG. 2A with the jaw members disposed in an approximated position and with the knife blade disposed in an extended position.

Referring now to FIGS. 2A-2C, in conjunction with FIG. 1, the use and operation of forceps 10 will be briefly described. As shown in FIG. 2A, jaw members 110, 120 of end effector assembly 100 are initially disposed in the spaced-apart position. In this position, as mentioned above, moveable handle 40 is disposed in the initial, spaced-apart position relative to fixed handle 50. In use, end effector assembly 100 is maneuvered into position such that tissue to be grasped, sealed, and/or divided, is disposed between jaw members 110, 120. Next, moveable handle 40 is pulled proximally relative to fixed handle 50 such that jaw member 110 is pivoted relative to jaw member 120 from the spaced-apart position to the approximated position to grasp tissue therebetween (see FIG. 2B). More specifically, as moveable handle 40 is pulled proximally, drive bar 130 (FIGS. 3B-3C) is translated relative to end effector assembly 100 to urge jaw member 110 to rotate about pivot 103 from the spaced-apart position to the approximated position. Thereafter, electrosurgical energy may be supplied, e.g., via activation of switch 90 (FIG. 1), to tissue-sealing plate 112 and/or tissue-sealing plate 122 and conducted through tissue to effect a tissue seal. As shown in FIG. 2C, knife blade 182 may then be advanced from the retracted position (FIG. 2B) to the extended position (FIG. 2C), e.g., via activation of trigger 82 of trigger assembly 80 which, in turn, advances knife bar 184 through shaft 12 to advance knife blade 182 through blade channels 115, 125 of jaw members 110, 120, respectively, to cut the previously sealed tissue grasped between jaw members 110, 120 (or to cut untreated tissue, depending on a particular purpose). Finally, moveable handle 40 may be returned to the initial position, translating drive bar 130 (FIGS. 3B-3C) relative to end effector assembly 100 such that jaw member 110 is urged to pivot back to the spaced-apart position.

Figure 3A:
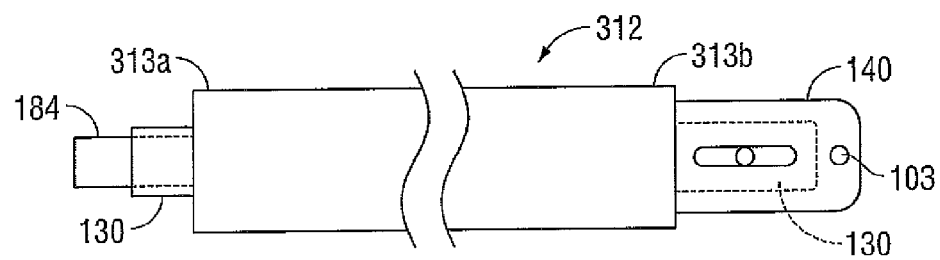
FIG. 3A is a side view of one embodiment of a shaft configured for use with the forceps of FIG. 1.
Figure 3B:
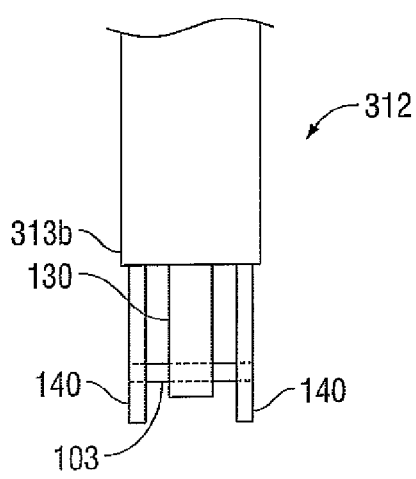
FIG. 3B is a top view of the shaft of FIG. 3A.
Figure 3C:
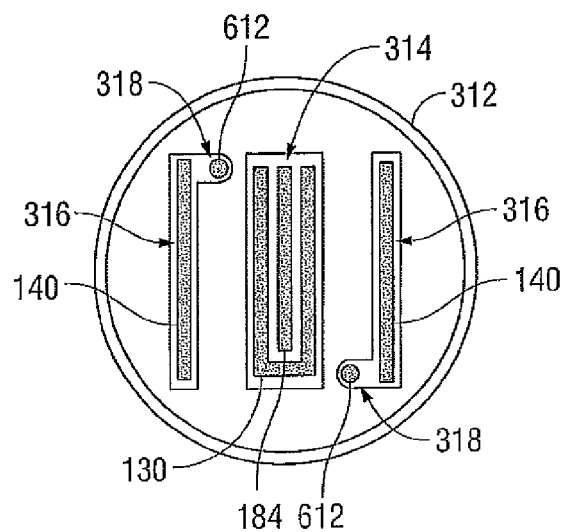
FIG. 3C is a transverse, cross-sectional view of the shaft of FIG. 3A.

Turning now to FIGS. 3A-3C, one embodiment of a shaft 312 configured for use with forceps 10 is shown. Shaft 312 defines a generally cylindrically-shaped configuration, although other configurations are contemplated, and may be formed from any suitable biocompatible material, e.g., plastics or other suitable polymeric materials. Plastics may be particularly suitable in that they are insulative, thus electrically insulating the internal components of shaft 312 from one another and from the external environment. As can be appreciated, forming the shaft 312 from an insulative material obviates the need to otherwise electrically insulate the shaft 312.

With continued reference to FIGS. 3A-3C, and particularly with reference to FIG. 3C, shaft 312 includes a plurality of lumens, although the number and/or configuration of the lumens extending through shaft 312 may be varied as desired, depending on the particular surgical instrument and/or end effector assembly used in conjunction with shaft 312. As shown in FIGS. 3A-3C, shaft 312 includes a central lumen 314 extending longitudinally therethrough. Central lumen 314 is generally rectangular-shaped, although other configurations may be provided. Central lumen 314, as will be described in greater detail below, is configured to house drive bar 130 of the drive assembly and knife bar 184 and knife blade 182 of knife assembly 180 (FIG. 2A-2C), which are selectively translatable through shaft 312 and relative to end effector assembly 100 to move jaw members 110, 120 between the spaced-apart and approximated positions and to advance knife blade 182 between jaw members 110, 120 to divide tissue grasped therebetween, respectively. As can be appreciated, in order to effect movement of jaw members 110, 120 and/or advancement of knife blade 182 via manipulation of moveable handle 40 (FIG. 1) and trigger 82 (FIG. 1), respectively, drive bar 130 and knife bar 184 extend through shaft 312 from the proximal end 313a thereof, i.e., from housing 20, to the distal end 313b thereof, i.e., to end effector assembly 100, thereby coupling the user-controls, e.g., moveable handle 40 and trigger 82, to end effector assembly 100.

Shaft 312 further includes a pair of offset lumens 316 extending longitudinally through shaft 312. Offset lumens 316 are generally rectangular in shape and each include a wire lumen 318 in communication therewith, although wire lumens 318 may alternatively be independent of offset lumens 316. Wire lumens 318 likewise extend through shaft 312, i.e., from the proximal end 313a to the distal end 313b thereof, and are configured to receive wires 612 of cable 610 (FIG. 1) therein such that, as mentioned above, electrosurgical energy may be transmitted via wires 612 from the source of energy (e.g., a generator, battery, or other suitable energy source), through shaft 312, to seal plates 112, 122 of jaw members 110, 120, respectively, to seal tissue grasped therebetween.

Each of the offset lumens 316, on the other hand, is configured to retain a proximal portion of a mounting flange 140 therein. Mounting flanges 140, as shown in FIGS. 3A and 3B, in conjunction with FIG. 1, are fixed in position relative to shaft 312 and extend distally from shaft 312. Mounting flanges 140 also engage pivot pin 103 therebetween, which rotatably couples jaw members 110, 120 to one another. Further, in embodiments where end effector assembly 100 is designed as a unilateral assembly, i.e., as shown in FIG. 1, jaw member 120 may be fixedly engaged to one or both of mounting flanges 140, while jaw member 110 is moveable relative thereto between the spaced-apart and approximated positions, or, in bilateral embodiments, jaw members 120 may simply be rotatably coupled to mounting flanges 140. In either configuration, mounting flanges 140 are secured within offset lumens 316 via any suitable mechanism, e.g., adhesion, friction-fit, etc. Shaft 312 may further include an outer sleeve (similar to outer sleeve 414 of shaft 412 (see FIGS. 4A-4C)) disposed about shaft 312. The outer sleeve may be formed from a metal or other suitable biocompatible material to add additional support to shaft 312.

With continued reference to FIGS. 3A-3C, the manufacture of shaft 312 and the components thereof will be described. Initially, shaft 312 is formed, e.g., using biocompatible plastic or other suitable material, via extrusion, to form the desired configuration of shaft 312, e.g., to form central lumen 314, offset lumens 316 and wire lumens 318. Extrusion is advantageous in that complex cross-sectional configurations may be created through a relatively inexpensive process. In other words, extrusion allows the formation of central lumen 314, offset lumens 316 and wire lumens 318, or any other number and/or configuration of lumens, while the remainder of shaft 312 remains solid. Such a process allows the lumens to be specifically configured for their intended purpose while the otherwise solid shaft 312 provides added structural support as compared to a hollow shaft.

Continuing with reference to FIGS. 3A-3C, in conjunction with FIG. 1, the formation of the components disposed within shaft 312, e.g., drive bar 130, knife bar 184 and mounting flanges 140, is described. One or more of these components may be formed from a metal, or other suitable material, via stamping, another relatively inexpensive process. Stamping is also advantageous in that specific features, e.g., grooves, pivot holes, cam slots, etc. may be subsequently or simultaneously formed through the stamped components, as desired. Further, although the stamping process yields relatively thin metal components, the configuration of lumens 314, 316 (through which drive bar 130 and knife bar 184 and mounting flanges 140, respectively, are to be inserted) constrains the components within shaft 312, thereby inhibiting buckling, when loaded in compression, and/or substantial twisting, when subject to torsional loading. In other words, during the extrusion process, the lumens extending through shaft 312 and the stamped components to be inserted therein are formed complementary in cross-section to one another to support and provide additional strength to the stamped components during use.

As best shown in FIG. 3C, drive bar 130 defines a U-shaped configuration (although other configurations may be provided) and is constrained by the internal dimensions of lumen 314. Similarly, knife bar 184 and knife blade 182 (FIGS. 2A-2C) are disposed within the dimensions of U-shaped drive bar 130 and, thus are similarly limited by the internal dimensions of lumen 314 as well as by U-shaped drive bar 130. Accordingly, smooth and consistent translation of drive bar 130 and knife bar 184 and knife blade 182 to move jaw members 110, 120 between the spaced-apart and approximated positions and to cut tissue grasped between jaw members 110, 120, respectively, are achieved. Likewise, lumens 316 retain mounting flanges 140 therein and provide support to mounting flanges 140, which mount jaw members 110, 120 thereon. Lumens 318, on the other hand, provide a portal through which wires 612 may be fed to electrically couple seal plates 112, 122 of jaw members 110, 120, respectively, to the source of energy (not explicitly shown) and help prevent wires 612 from catching on, interfering with, or being damaged by the other components of shaft 312.

Figure 4A:
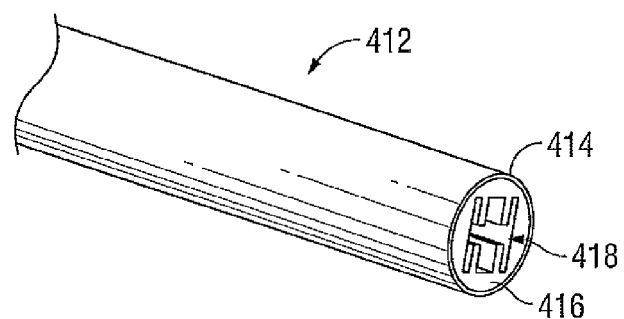
FIG. 4A is a front, perspective view of another embodiment of a shaft configured for use with the forceps of FIG. 1.
Figure 4B:
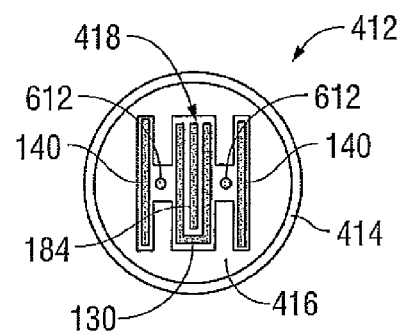
FIG. 4B is a transverse, cross-sectional view of the shaft of FIG. 4A.
Figure 4C:
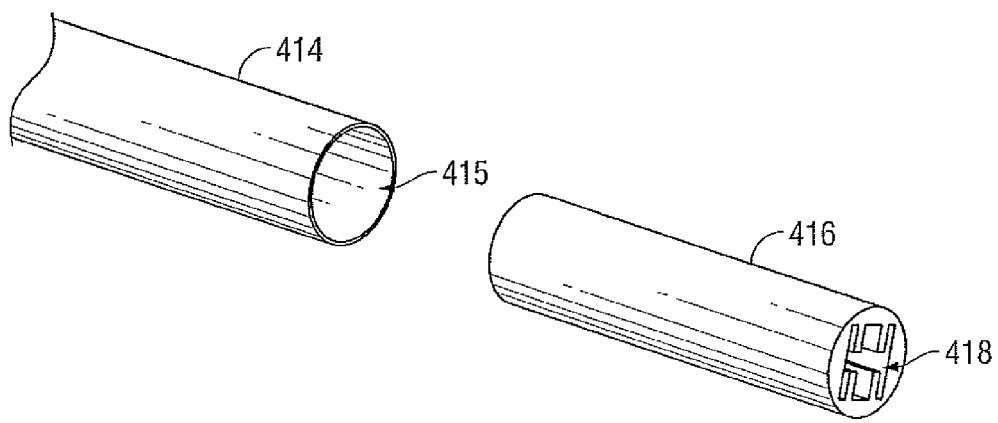
FIG. 4C is an exploded view of the shaft of FIG. 4A.

Turning now to FIGS. 4A-4C, another embodiment of a shaft 412 configured for use with forceps 10 or any other suitable surgical instrument is shown. Shaft 412 is similar to shaft 312 (see FIGS. 3A-3C) and, thus, for purposes of brevity, will only be summarized hereinbelow, keeping in mind that the features and operation of shaft 312 described above apply similarly to shaft 412. Further, the additional features identified below with respect to shaft 412 are similarly applicable to shaft 312.

Continuing with reference to FIGS. 4A-4C, shaft 412 includes an outer sleeve 414 formed from a metal, or other suitable biocompatible material that provides support and strength to shaft 412. Outer sleeve 414 defines a hollow configuration having a longitudinal passageway 415 extending therethrough. Longitudinal passageway 415 of outer sleeve 414 defines a cylindrical configuration and, thus, a circular cross-sectional configuration, although other configurations are contemplated. An inner shaft 416 is disposed within longitudinal passageway 415 of outer sleeve 414. Inner shaft 416 is formed from a plastic or other suitable material and may be electrically insulative. Inner shaft 416 defines an outer cross-sectional configuration and outer diameter that are substantially similar to the diameter and cross-sectional configuration of longitudinal passageway 415 such that, when inner shaft 416 is positioned within outer sleeve 414, inner shaft 416 substantially fills the volume of passageway 415, as best shown in FIG. 4A, forming a strong, stable shaft 412. Inner shaft 416 may be secured within outer sleeve 414 via any suitable method, e.g., friction-fit, adhesion, etc.

Referring now to FIG. 4B, inner shaft 416 includes a lumen 418 extending therethrough. Lumen 418 defines a specific cross-sectional configuration different from the cross-sectional configuration of passageway 415 of outer sleeve 416. Inner shaft 416 is formed from molding, e.g., insert molding, injection molding, or other suitable process. Molding is advantageous in that it is a relatively inexpensive process that allows the formation of complex-shaped lumens extending through inner shaft 416, e.g., lumen 418. Further, the configuration of shaft 412 allows the metal outer sleeve 414 to be formed simply (an inexpensively) as a cylindrical, tube-like structure for adding support to shaft 412, while inner shaft 416 is formed from a plastic and includes multiple and/or complexly-shaped lumens 418 extending therethrough for receiving various (and differently-configured) components therein. In particular, lumen 418 may be configured to retain mounting flanges 140, drive bar 130, knife bar 184 and wires 612 therein, either in a single lumen 418, or, similar to shaft 312, via multiple lumens. In either configuration, the lumen(s) 418 are specifically configured to retain the components of the surgical instrument therein to facilitate the use and operation of end effector assembly 100 (FIG. 1) via controls disposed remotely therefrom (e.g., moveable handle 40, trigger 82, and/or activation switch 90 (see FIG. 1)).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing a surgical instrument, comprising:
    forming a shaft via extrusion such that the shaft includes a plurality of lumens extending therethrough including a drive lumen and at least one support lumen;
    forming, via stamping, a drive component that is shaped complementary to the drive lumen;
    inserting the drive component into the drive lumen;
    forming, via stamping, at least one support flange component that is shaped complementary to the at least one support lumen; and
    inserting the at least one support flange component into the at least one support lumen.

2. The method according to claim 1, further comprising coupling an end effector assembly to the at least one support flange component.

3. The method according to claim 2, wherein the drive component is a drive bar slidably disposed within the drive lumen, and wherein the method further comprises operably engaging the drive bar with the end effector assembly such that translation of the drive bar through the drive lumen effects movement of the end effector assembly between a first condition and a second condition.

4. The method according to claim 2, wherein the shaft is formed to include at least one electrical connection lumen, and wherein the method further comprises
    inserting at least one electrical wire through the at least one electrical connection lumen and coupling the at least one electrical wire to the end effector assembly.

5. The method according to claim 1, further comprising positioning the shaft within an outer sleeve.

6. The method according to claim 5, further comprising forming the shaft from an electrically-insulative material and forming the outer sleeve from an electrically-conductive material.

* * * * *